(12) United States Patent
Curran

(10) Patent No.: US 12,079,199 B2
(45) Date of Patent: *Sep. 3, 2024

(54) METHODS AND APPARATUS TO REDUCE THE IMPACT OF USER-ENTERED DATA ERRORS IN DIABETES MANAGEMENT SYSTEMS

(71) Applicant: Ascensia Diabetes Care Holdings AG, Basel (CH)

(72) Inventor: Kevin Curran, Wayne, NJ (US)

(73) Assignee: Ascensia Diabetes Care Holdings AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/471,795

(22) Filed: Sep. 21, 2023

(65) Prior Publication Data
US 2024/0012806 A1    Jan. 11, 2024

Related U.S. Application Data

(63) Continuation of application No. 15/268,517, filed on Sep. 16, 2016, now Pat. No. 11,803,534.

(Continued)

(51) Int. Cl.
*G06F 16/23* (2019.01)
*G06F 16/215* (2019.01)
(Continued)

(52) U.S. Cl.
CPC ........ *G06F 16/2365* (2019.01); *G06F 16/215* (2019.01); *G06F 16/22* (2019.01);
(Continued)

(58) Field of Classification Search
CPC ............ G06F 16/2365; G06F 16/2329; G06F 16/2336; G06F 16/22; G06F 16/2379;
(Continued)

(56) References Cited

U.S. PATENT DOCUMENTS

| | | | |
|---|---|---|---|
| 2010/0094648 A1* | 4/2010 | Seward ................. | G16H 50/70 705/2 |
| 2013/0304499 A1* | 11/2013 | Rangadass ..... | G06Q 10/063114 705/2 |
| 2016/0378752 A1* | 12/2016 | Anderson ........... | G06F 16/2255 707/747 |

OTHER PUBLICATIONS

European Patent Application 16777946.1 Intent to Grant issued May 8, 2024.

* cited by examiner

*Primary Examiner* — Hosain T Alam
*Assistant Examiner* — Lin Lin M Htay
(74) *Attorney, Agent, or Firm* — Erise IP, P.A.

(57) ABSTRACT

Embodiments provide systems, methods, and apparatus for reducing the impact of user-entered data errors in a data management system (DMS) such as for diabetes. Embodiments include storing user-entered data received from a user into a primary DMS database; storing secondary data received from a source other than the user into a secondary tracking database; associating the secondary data with one or more events described by the user-entered data; cross-checking the user-entered data against the associated secondary data; evaluating user-entered data based on the cross-checking results; presenting for review evaluated user-entered data; treating user-entered data in the primary DMS database based on review results; and determining a diabetes management plan based on the treated user-entered data. Numerous other aspects are provided.

19 Claims, 4 Drawing Sheets

Related U.S. Application Data

(60) Provisional application No. 62/234,490, filed on Sep. 29, 2015.

(51) Int. Cl.
  *G06F 16/22* (2019.01)
  *G16H 10/60* (2018.01)
  *G16H 40/63* (2018.01)
  *G16H 40/67* (2018.01)
  *G16Z 99/00* (2019.01)

(52) U.S. Cl.
  CPC ...... *G06F 16/2308* (2019.01); *G06F 16/2315* (2019.01); *G06F 16/2322* (2019.01); *G06F 16/2329* (2019.01); *G06F 16/2336* (2019.01); *G06F 16/2343* (2019.01); *G06F 16/2379* (2019.01); *G16H 10/60* (2018.01); *G16H 40/63* (2018.01); *G16H 40/67* (2018.01); *G16Z 99/00* (2019.02)

(58) Field of Classification Search
  CPC ............... G06F 16/2343; G06F 16/215; G06F 16/2308; G06F 16/2315; G06F 16/2322; G16H 40/67; G16H 10/60; G16H 40/63; G16Z 99/00
  See application file for complete search history.

400

Primary DMS DB

| Time Stamp 402 | Event 404 | State 406 | Associated 2ndary Event ID 408 | Weight 410 | |
|---|---|---|---|---|---|
| 1:02 PM | Pre-Meal Marker | Unverified | 123 | 1.0 | 412 |
| 4:30 PM | Exercise for 30 mins | Suspect | 456 | 0.5 | 414 |
| 8:00 PM | Sleep | Invalidated | 789 | 0.0 | 416 |
| | | | | | |

Secondary Tracking DB

| Time Stamp 502 | Secondary Event ID 504 | Secondary Event 506 | Data Source 508 | |
|---|---|---|---|---|
| 1:09 PM | 123 | Eating food | Neck-worn eating sensor | 510 |
| 4:05 PM | 456 | HR>130 for 45 mins | HRM | 512 |
| 8:20 PM | 789 | Walking for 1 hour | Pedometer | 514 |
| | | | | |

FIG. 5

METHODS AND APPARATUS TO REDUCE THE IMPACT OF USER-ENTERED DATA ERRORS IN DIABETES MANAGEMENT SYSTEMS

RELATED APPLICATIONS

This patent application is a continuation application claiming priority benefit, with regard to all common subject matter, of U.S. patent application Ser. No. 15/268,517, filed Sep. 16, 2016, and entitled "METHODS AND APPARATUS TO REDUCE THE IMPACT OF USER-ENTERED DATA ERRORS IN DIABETES MANAGEMENT SYSTEMS" ("the '517 application"). The '517 application claims priority benefit, with regard to all common subject matter, of U.S. Provisional Patent Application No. 62/234,490, filed Sep. 29, 2015, and entitled "SYSTEMS, METHODS AND APPARATUS FOR GENERATING MEAL MARKERS BASED ON SENSOR DATA." The identified earlier-filed patent applications are hereby incorporated by reference in their entirety into the present application.

FIELD

Embodiments of the present invention relate to data management systems, more specifically diabetes management systems and methods, and more specifically to methods and apparatus to reduce the impact of user-entered data errors in such systems.

BACKGROUND

Diabetes mellitus is a serious, life-long disorder that is, as yet, incurable. Each year in the U.S. alone, about 2 million people are diagnosed with diabetes, the 7th leading cause of death in the United States. In 2012, 86 million Americans age 20 and older had pre-diabetes; this is up from 79 million in 2010. In 1993, there were approximately eight million diagnosed cases of diabetes mellitus in the United States, and the number has grown to about 21 million currently diagnosed cases. In addition, there are at least 8 million undiagnosed cases.

The effects from diabetes on the healthcare system are startling. In the U.S., the cost of hospitalizations, supplies, lost work, disability payments, and premature deaths from diabetes reached more than $245 billion in 2012 alone. In addition, the long-term complications associated with diabetes, particularly when poorly managed, can lead to serious financial and human consequences. Serious diabetes-related complications, including cardiovascular disease, kidney disease, nerve damage, blindness, circulatory problems (which can lead to amputations), stroke, heart disease and pregnancy complications, are estimated to cost more than $176 billion annually. Some health maintenance organizations estimate that while only 3.1% of their covered patients have diabetes, diabetic patients account for over 15% of their total healthcare costs.

Research conducted by the National Institute of Health has shown that if people with diabetes closely monitor and control their blood glucose levels, they will enjoy significant health benefits. Consistent management of diabetes, which includes diet, exercise, and aggressive monitoring and control of blood glucose levels, can lessen the risk of serious complications and potentially reduce some diabetes-related conditions by more than half.

The study further revealed that active management of diabetes could, among other benefits, reduce eye disease by up to 76%, reduce kidney disease by up to 50%, and reduce nerve disease by up to 60%. Furthermore, treatment regimens necessitate tightly controlled glucose levels within a lower, healthier range, which inherently cause an increased risk of more frequent hypoglycemic episodes, if the level drops too low, below the range. A very real issue facing many diabetics is the possibility of falling into a hypoglycemic coma, or experiencing other diabetic emergencies, without external assistance. Likewise, the risk of a diabetic emergency in a child or other dependent confronts many parents and guardians of diabetic individuals. The possibility of a diabetic emergency may hinder both the diabetic individual and the guardian from leading active, independent lifestyles. Thus, what are needed are improved diabetes management systems and methods. Likewise, diabetes management systems often rely on user-entered data in controlling blood glucose levels, and user-entered data can introduce user-based data errors, which can undermine the reliability of the data in general as well as the reliability of the diabetes management system to control blood glucose levels. Therefore, systems and methods are needed to improve the reliability of management systems relying on user-entered data, and the data in general relied upon therein.

SUMMARY

In some embodiments, a method for reducing the impact of user-entered data errors in a data management system (DMS), such as a diabetes management system, is provided. The method includes storing user-entered data received from a user into a primary DMS database; storing secondary data received from a source other than the user into a secondary tracking database; associating the secondary data with one or more events described by the user-entered data; cross-checking the user-entered data against the associated secondary data; marking the user-entered data for review based on the cross-checking results; presenting marked user-entered data for review; updating user-entered data in the primary DMS database based on review results; and determining a diabetes management plan based on the updated user-entered data.

In other embodiments, a data management system (DMS), such as a diabetes management system, is provided. The system includes a DMS device adapted to execute a DMS application; at least one sensor assembly in communication with the DMS device; a primary DMS database accessible by the DMS application; and a secondary tracking database accessible by the DMS application. The DMS device includes a processor coupled to a memory and the memory is operative to store instructions executable on the processor to: store user-entered data received from a user into the primary DMS database; store secondary data received from the at least one sensor assembly into the secondary tracking database; associate the secondary data with one or more events described by the user-entered data; cross-check the user-entered data against the associated secondary data; mark user-entered data for review based on the cross-checking results; present the marked user-entered data for review; update the user-entered data in the primary DMS database based on review results; and determine a diabetes management recommendation based on the updated event data.

In still other embodiments, an apparatus for generating secondary data for reducing the impact of user-entered data errors in a data management system (DMS), such as a diabetes management system, is provided. The apparatus includes a sensor assembly, which may be adapted to be worn on a user's body, the sensor assembly including a transceiver operable to transmit measured secondary data to a DMS device executing a DMS application. The non-user-entered secondary data could be clock data from a BGM or a set of parameters stored in the device (e.g., if user enters calorie intake as 20,000 calories, that may be contrary to a parameter maximum number of calories). The DMS application is operative to store the secondary data in a secondary data tracking database, associate the stored secondary data with user-entered data in a primary DMS database, and cross-check the user-entered data against the secondary data to identify incorrect or inconsistent user-entered data for review.

Numerous other aspects are provided in accordance with these and other aspects of the invention. Other features and aspects of the present invention will become more fully apparent from the following detailed description, the appended claims and the accompanying drawings.

BRIEF DESCRIPTION OF THE DRAWING FIGURES

FIG. 4 is a tabular representation of a first example database according to embodiments of the present invention.

FIG. 5 is a tabular representation of a second example database according to embodiments of the present invention.

DETAILED DESCRIPTION

Figure 1:
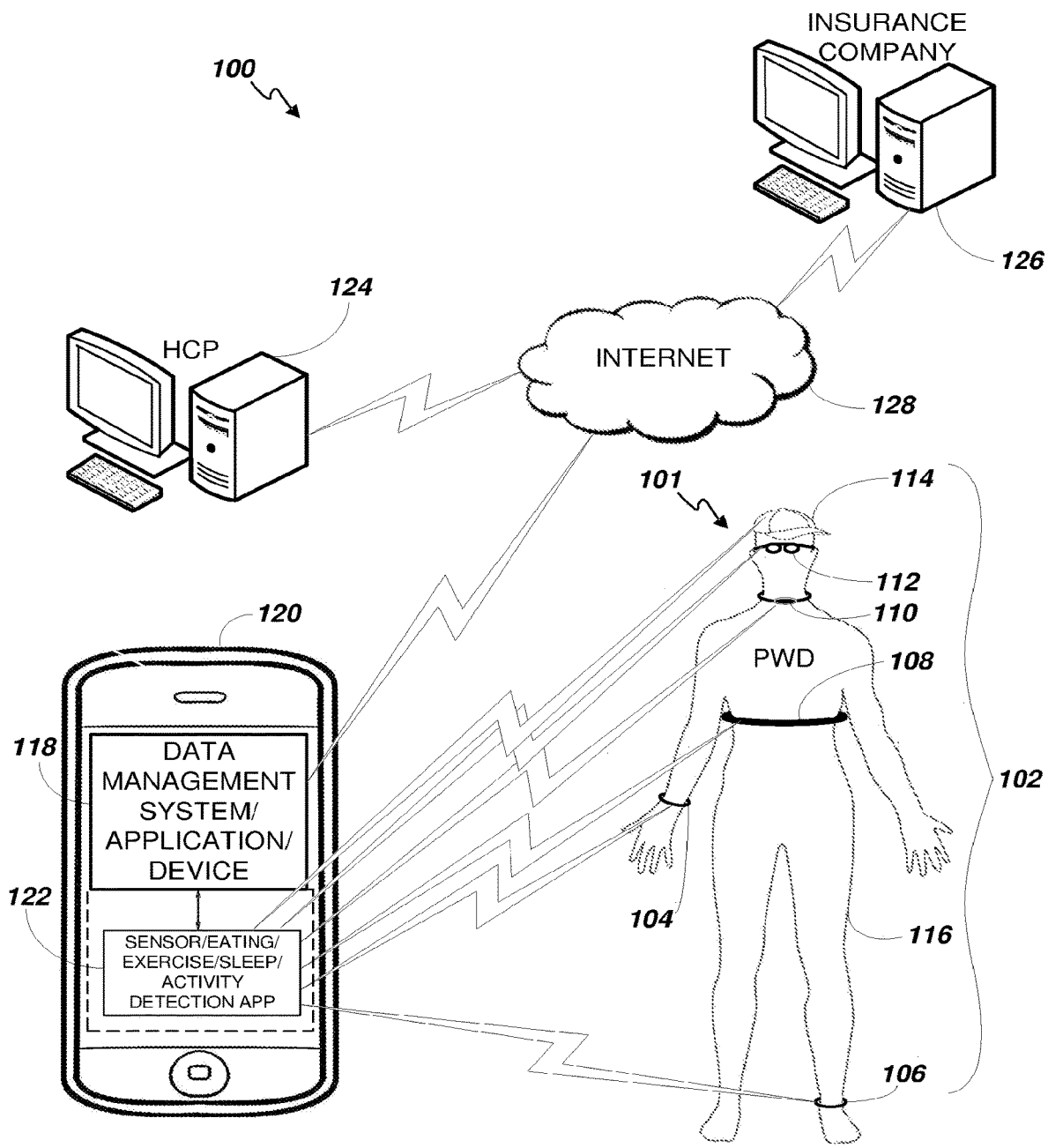
FIG. 1 is a schematic block diagram depicting an example diabetes management system according to embodiments of the present invention.

For the purposes of promoting an understanding of the principles of embodiments of the invention, reference will now be made to the examples illustrated in the drawings and specific language will be used to describe the same. It will nevertheless be understood that no limitation of the scope of the invention is thereby intended, and any alterations and further modifications in the illustrated embodiments, and any further applications of the principles of the invention as illustrated therein as would normally occur to one skilled in the art to which the invention relates are contemplated herein.

Embodiments of the present invention provide systems, apparatus and methods for an improved data management system (DMS), such as a diabetes management system that includes features adapted to reduce the impact of user-entered data errors on determinations made based on a collection of data that includes the user-entered data errors. In other words, in some embodiments, the present invention provides systems, methods and apparatus adapted to reduce the impact of user-entered data errors in a DMS, and thereby achieve a more reliable and less error-containing dataset within a DMS. In some embodiments of the invention, the results could include improved tracking of meals and other events relevant to managing glucose levels, such as exercise, sleep, and medication taken or administered. Relevant events conventionally have been tracked in a database by a user manually entering the event data directly into the database, such as giving a blood glucose meter (BGM) reading a meal marker to indicate, for instance, whether the meter reading occurred before or after a meal. These user-entered data may be considered to reside in a primary DMS database, data from which may be visible to the user. Embodiments of the present invention may employ a secondary DMS database, e.g., referred to as a secondary tracking database, to supplement, validate (or invalidate), rate/weight, and/or flag data in the primary DMS database. Via the use of a secondary tracking database, additional data about events tracked in a primary DMS database can be captured and cross-checked against event data in the primary DMS database. In some embodiments, the additional "secondary data" can be used to generate a confidence rating of individual entries in the primary DMS database (which can be used for example to determine a weighting for the event data). In addition, the additional secondary data can be used to provide an indication that a primary DMS database entry should be verified or appears to conflict with other data from an alternate source such as, e.g., an automated monitoring system such as an on-body sensor assembly.

Secondary data may range in complexity and originate from various different sources, including from a BGM itself. For instance, a user may take a BGM reading at 10 am and mark the BGM reading with a 'pre-meal' marker. However, inasmuch as a 'pre-meal' marker is intended to be used only when a meal occurs at most 30 minutes after the BGM reading, a reading taken at 10 am may be outside of the user's normal 'pre-meal' range of 11:30 am-12:00 pm if the user typically eats lunch at noon. In some embodiments of the present invention, this 10 am time value for a reading being outside the user's normal behavior may be regarded as sufficient to bring the 'pre-meal' marker into question. The suspect nature of this 10 am 'pre-meal' marker may be compounded if the blood glucose (BG) value is not in line with typical pre-meal BG values, and/or a later BGM reading taken at 2:30 pm is marked as with a 'post-meal' marker, which generally is to be assigned not more than two hours after the start of a meal, placing the presumptive start of the meal at no earlier than 12:30 pm. Thus, based on data stored in the primary DMS database, a ruleset can be defined to identify suspect data and flag the suspect data to be reviewed and/or corroborated. In some embodiments, a ruleset can be used to generate secondary tracking data from the primary DMS DB which can then be cross-checked against, used to validate (or invalidate), weight, or flag user-entered data in the primary DMS DB.

Other data available to the DMS, such as food/meal/calories consumption entries, either from another system, application, or entered directly into the DMS, may also be used to cross-reference or cross-check user-entered data (e.g., the 'pre-meal' marker), and either support or undermine the credibility of the user-entered data. For instance, both the absence of a calorie entry within the 'pre-meal' window of time, and the possible existence of a calorie entry somewhat beyond the 'pre-meal' window of time, can be used as a rule to allow the DMS to undermine the credibility of the 'pre-meal' marker. Conversely, a calorie entry within the 'pre-meal' window of time would allow the DMS to support or validate the credibility of the 'pre-meal' marker. Moreover, if a pattern of gaps in user-entered data arises, the pattern of gaps may be used by the DMS to explain away and reduce the credibility-undermining nature of an absence of user-entered data, such as where the user fails to enter a calorie consumption entry after applying a 'pre-meal' marker, but where such an absence is not uncommon for the user and where the user otherwise fails to enter all calories consumed. In some embodiments, a secondary tracking database and a secondary analysis ruleset can be used to perform a balancing analysis in which various factors are included in assessing the credibility of user-entered data, with any given factor supporting, undermining, or not impacting the credibility of the user-entered data. In other words, based on the outcome of the balancing, the DMS can decide to devalue the data, increase the value of the data, ignore the data, or not alter the value of the data in making diabetes management recommendations or suggestions.

The secondary tracking database may be used by a DMS in several ways, either individually or in combination with each other. In some embodiments, missing data or gaps in the primary DMS database can be filled by simply supplementing the data, either automatically, or via user confirmation of the substitute supplemental secondary tracking data. In some other embodiments, the secondary tracking data can be used as a basis for comparison against the primary DMS database in order to validate the primary data, possibly in the background without being visible to the user, or to invalidate the primary data, either by default, by suggestion to the user with confirmation by the user, or by flagging the primary data to await review by the user. A further embodiment can use the secondary tracking database to generate an alternative dataset used as a factor in error compensation calculations, either for individual meter readings, or for pattern detections/calculations (e.g., X is the original value or pattern from the primary DMS database, and X' is the revised value or pattern after error compensation using the secondary tracking database). Similarly, if individual values are revised, any pattern derived from such revised values semantically would be a revised pattern, compared to the original pattern, even if the revised pattern did not differ from the original pattern.

Many different types of situations/events can give rise to secondary data tracked in the secondary tracking database. For example, if a user wearing a heart rate monitor (e.g., a FitBit® wrist-worn device) manually enters into a DMS application that he exercised for 30 minutes starting at 3 PM on Thursday, but the heart rate monitor (HRM) separately reports to the DMS application that the exercise period was actually 40 minutes starting at 2:45 PM, embodiments of the present invention can store the data from the heart rate monitor in a secondary tracking database, associate it with the manually entered information in the primary DMS DB, and flag the user-entered event data in the primary DMS DB as possibly inaccurate. The association between the user-entered event data and the event data from the HRM can also be stored in the primary DMS DB and a request for verification of the user-entered data can be stored for future presentation to the user. The request can include an indication of the system's basis for questioning the primary data to help the user decide for example, whether to validate, invalidate, or replace the primary data. For instance, the request can be presented as a question to the user on the display of a smartphone executing the DMS application: "You indicated you exercised for 30 minutes starting at 3 PM on Thursday but your HRM reported you exercised for 40 minutes starting at 2:45 PM. Would you like to keep the original information, use the HRM information, or edit the information?" In some embodiments, the DMS can then ask the user if similar future requests should be handled in the same manner automatically. For example, the user can choose to always defer to data from the HRM.

Likewise, pre- and post-meal markers manually entered by a user into a BGM and later transferred to a DMS application can be stored in a primary DMS database and be later cross-checked against BGM testing data (e.g., the results of the cross-check to be stored in a secondary tracking database) to determine if any inconsistencies indicated possible errors or a potential need to verify data. For example, if a user entered a "pre-meal" marker into a DMS application, but the associated BGM test data more closely corresponds to blood glucose levels historically associated with "post-meal" BGM readings, the pre-meal marker could be flagged as a possible error and/or the BGM test data could be flagged as possibly inaccurate. Further, if for example, the user was wearing a sensor that can detect the consumption of food (e.g., See: https://www.mdtmag.com/news/2015/03/necklace-and-smartphone-app-can-help-track-food-intake?et_cid=4463079&et_rid=651698069&type=cta and "Recognition of Nutrition Intake Using Time-Frequency Decomposition in a Wearable Necklace Using a Piezoelectric Sensor", IEEE SENSORS JOURNAL, VOL. 15, NO. 7, pp. 3909-3916, July 2015) (both of which are incorporated herein by reference), the timing of the meal marker can be verified/invalidated and/or the BGM test data can be further called into question.

In some embodiments, instead of outright invalidating data, the suspect data can be flagged for future review and/or de-weighted (e.g., pending user review) so as to have less influence on an overall evaluation of accuracy of event tracking. Event data in the primary DMS database can be evaluated against data in the secondary tracking database on an ongoing basis, and/or after a fixed amount of time or number of events, and/or at the convenience of the user or other person (e.g., a healthcare provider (HCP)) evaluating or reviewing the data. Embodiments of the invention thus enable reviewers to improve the accuracy of the data. For example, an HCP may be given the ability to toggle between viewing an original pattern (e.g., based solely on primary data in the primary database), and one or more revised patterns (e.g., based on the primary data in conjunction with various treatments of the secondary data), including a 'discrepancy' pattern that could highlight discrepancies between the primary data and the secondary data, and group the discrepancies according to size, over/underestimations, event types, event times, etc.

In some embodiments, a DMS application can provide a summary of the accuracy of the data in the primary DMS database based upon the number and types of apparent data inconsistencies between the event data in the primary DMS database and corresponding event data in the secondary tracking database. By reviewing a list and/or summary of apparent data inconsistencies, a user or HCP can more easily see patterns to identify and eliminate errors and thus, improve the accuracy of the data.

In some embodiments, the primary DMS database and the secondary tracking database can be implemented as separate databases that are correlated based on time or other indicia. The structure of the secondary tracking database could mirror the structure of the primary DMS in terms of content parameters. Moreover, the structure of the secondary tracking database could include data fields and values not found in the primary DMS database to reflect the additional sources of information, and include data that reflects the status and treatment of the secondary data. For instance, the secondary database may indicate that secondary data from event Y has been (1) suggested or not suggested to a user; (2) confirmed or not confirmed by a user; (3) replaces or does not replace related data in the primary DMS database; (4) supplements or does not supplement related data in the primary DMS database; (5) should or should not be used to compensate for errors in related data in the primary DMS database; etc. Furthermore, the secondary data may themselves create secondary patterns that may be tracked in the secondary database (e.g., secondary data may indicate that a user has a secondary pattern of overestimating durations of exercise by about Z %, potentially triggering a general pattern discounting user durations of exercise, even in cases where no secondary data are generated directly for an event to bring the accuracy of the primary data into question).

In other embodiments, the secondary database can be implemented by merely using additional fields, objects, and/or tables in the primary DMS database. In some embodiments, event data in the primary DMS database can have associated states that reflect the status of the event data. For example, the states can include unverified, verified, invalidated, to be reviewed, suspect, etc. "Unverified" can be used to indicate that the associated event data has not been verified but there is currently no reason to suspect the event data is not accurate. "Verified" can be used to indicate that the associated event data has been verified by a user or HCP. "Invalidated" can be used to indicate that the associated event data has been determined to be inaccurate or erroneous. "To be reviewed" can be used to indicate that there is a reason that the associated event data should be reviewed but that there is no clear indication that it is inaccurate or erroneous. "Suspect" can be used to indicate that the associated event data appears to be inaccurate or erroneous and thus should be reviewed. More or fewer states can be used. The states can have associated weights that reflect the relative significance of the associated event data given the respective state. Based on the amount of data in the respective states, an overall accuracy rating of the data can be determined and used to assess the suitability of the data for making healthcare decisions such as medicine dosage and diabetes management planning.

By tracking the secondary data, the system is creating a virtual "second opinion" on the accuracy of the primary data, by which a user, an HCP, or a DMS can improve the accuracy of the overall data collected and considered in management of a user's diabetes, hopefully leading to more effective diabetes management overall. For instance, improved and more accurate data could lead to better, more accurate calculations of insulin on-board, A1C levels, and/or insulin dosing regimens. For potential reasons of regulatory compliance and risk mitigation regarding liability for potentially inaccurate conclusions drawn from secondary data, the secondary data could be maintained independently of the original data and not overwrite or replace original data without the conscious confirmation and agreement of the user to overwrite or replace the original data, thereby placing on the user the onus, risk, and responsibility for such replacement and the accuracy of the secondary data. Similarly, a data audit trail may track the changes or reliance on user-entered data vis-a-vis the secondary data and establish the historical integrity of the user-entered data, especially user-entered data considered to contain errors.

Embodiments of the present invention are depicted in the example system 100 illustrated in FIG. 1. In some embodiments, a network 101 of on-body sensor assemblies 102, for example, as depicted in FIG. 1, can be embodied in, or implemented in the form of, wrist bands 104, ankle bands 106, chest straps 108, necklaces 110, eye glasses 112, hats 114, clothing (e.g., pants, shirt, vest, undergarments, jacket, etc.), sub-dermal implants, dental implants, ear buds, ear rings, rings, gloves, footwear, wig, etc. and be used to detect, measure and communicate (e.g., via wireless signals) physiological, positional, temporal, and biometric parameters of a user 116 (e.g., a person with diabetes (PWD)). Any number of on-body sensor assemblies 102 can be worn that are practicable. The on-body sensor assemblies 102 can wirelessly communicate with each other (e.g., using near field communication (NFC) or other low power signaling) and/or with a DMS application 118 implemented in a DMS device 120 such as a smartphone/tablet/laptop/etc., an artificial pancreas system, a BG meter, or any other suitable computing/processing device operable to execute the DMS application 118.

The DMS application 118 can receive activity or event data (e.g., data indicative of eating, sleeping, exercise, health condition, other activities, etc.) interpreted/identified by the on-body sensor assemblies 102 or from signals from the on-body sensor assemblies 102. In some embodiments, a separate detection application 122 can aggregate the raw signal data from the on-body sensor assemblies 102 and determine the patient's activities and condition.

In some embodiments, the DMS application 118 can determine a course of action based on the activity/condition information. In some embodiments, the information can be automatically (or with the user's permission) communicated to the patient's healthcare provider 124 (HCP) and/or insurance company 126, e.g., via a communications network such as the Internet 128, for a determination of the appropriate course of action.

Figure 2:
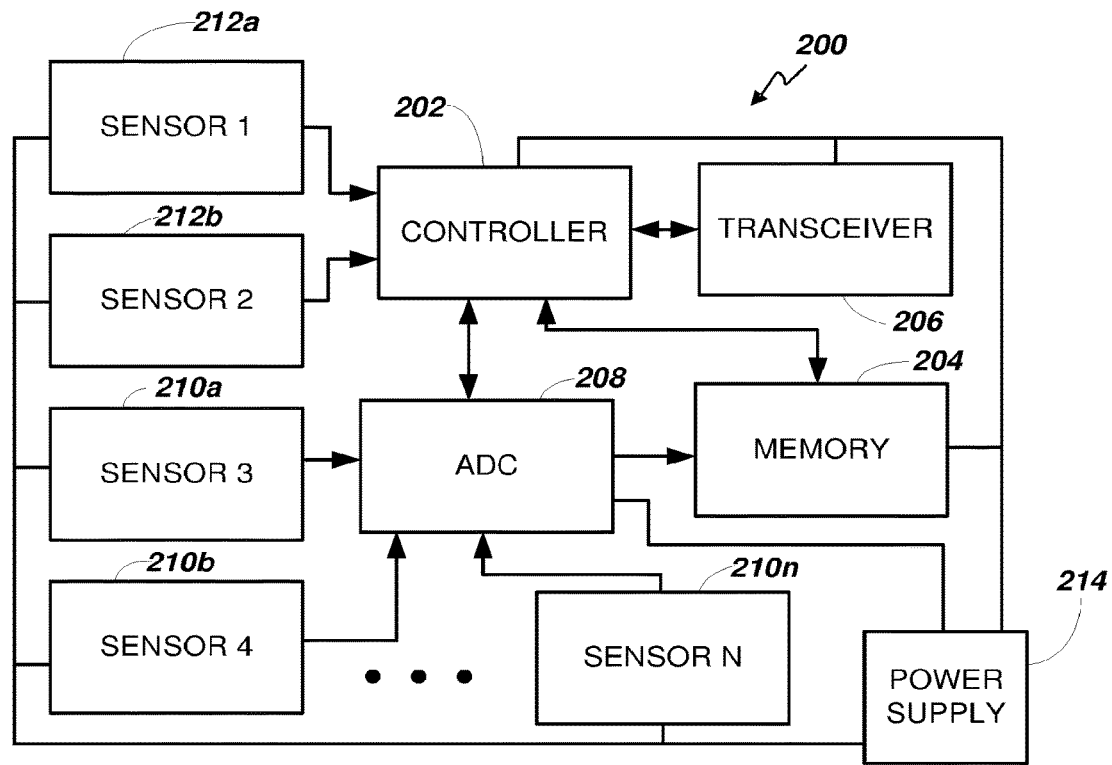
FIG. 2 is a schematic block diagram depicting an example on-body sensor assembly according to embodiments of the present invention.

Turning to FIG. 2, an example embodiment of an on-body sensor assembly circuit 200 is depicted. A controller 202 (e.g., a processor, a field programmable gate array (FPGA), etc.) is bi-directionally coupled to a memory 204 operative to store instructions executable on the controller 202. The controller 202 is also bi-directionally coupled to a transceiver 206 (e.g., a wireless transmitter/receiver) for two-way communication with other on-body sensors assemblies 102 and/or a DMS application 118 running on a DMS device 120 (e.g., a smartphone/tablet/PC/etc. or other device such as an artificial pancreas, BG meter, etc.).

The controller 202 is also bi-directionally coupled to an analog to digital converter (ADC 208) to be able to send control signals to the ADC 208 and to receive data signals from the ADC 208 from one or more connected sensors 210a-n. In some embodiments, the ADC 208 can include filters and/or signal conditioning circuitry. In some embodiments, the ADC 208 can store sensor data directly into the memory 204 as indicated by the line connecting the ADC 208 to the memory 204. In some embodiments, one or more sensors 212a-b can be coupled directly to the controller 202 (or via filters and/or signal conditioning circuitry) to provide sensor data signals. The controller 202 can store sensor or other data in the memory 204 (e.g., for processing or filtering) and/or immediately transmit the data via the transceiver 206. Each of the above components of the on-body sensor assembly circuit 200 can be coupled to a power supply 214 (e.g., a rechargeable battery) to receive power for operation.

The sensors 210a-n, 212a-b can include any type of sensor practicable to be worn on-body including sensors for measuring/detecting BG, other analytes, blood pressure, heart rate, pulse, wakefulness, breathing rate, respiration, body temperature, ambient temperature, pulse oximetry, humidity, electrocardiogram, movement, acceleration, proximity, direction, altitude, speed, applied force, pressure, perspiration, aging, sound, eating/drinking, snoring, weight, height, body composition (e.g., lean mass, body fat, etc.), etc. In addition, sensors for detecting specific medical or physiological conditions can be used. In some embodiments, sensors can be installed within the user's body (e.g., within a tooth filling, sub-dermally, within a body cavity, etc.); attached to skin with an adhesive (e.g., a patch); and/or held in place by clothing (e.g., via a vest or hat with built-in sensors).

Figure 3:
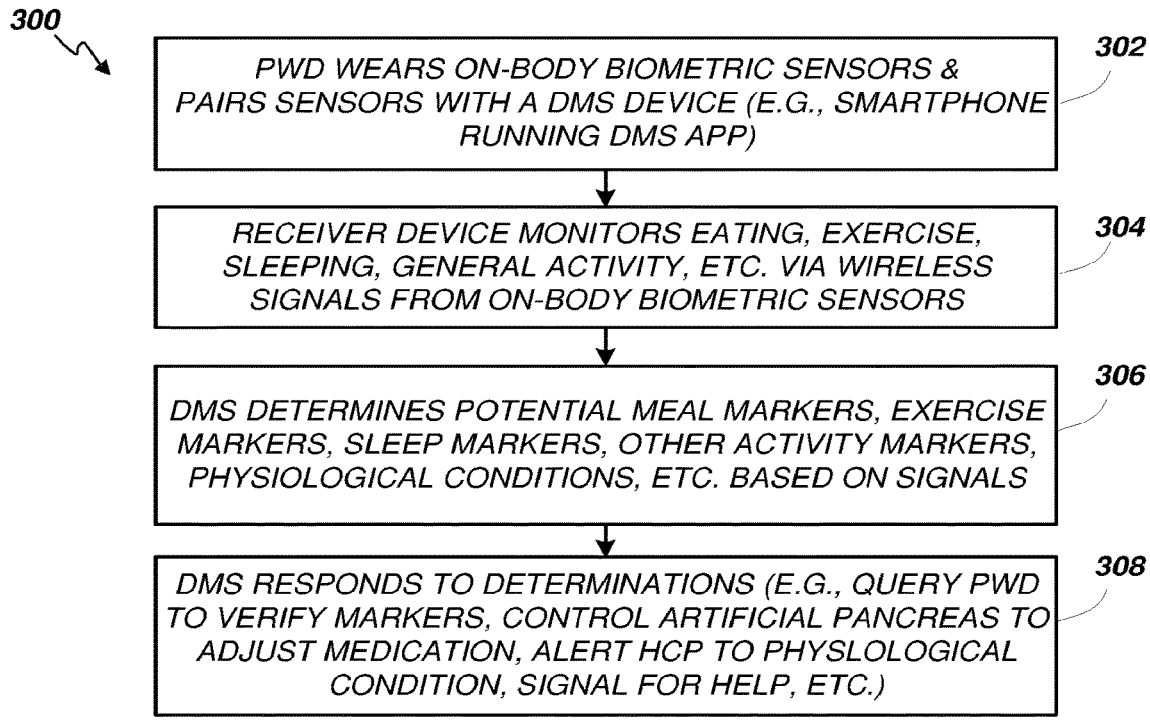
FIG. 3 is a flowchart depicting an example method of generating marker data based on sensor data according to embodiments of the present invention.

FIG. 3 depicts an example of a method 300 according to embodiments of the present invention. Initially a PWD wears one or more on-body sensor assemblies and establishes communication with a receiver such as a DMS device (302). The DMS device monitors eating, exercise, sleeping, other activities as well as a number of biometric and physiological parameters via wireless signals from the on-body sensor assemblies (304). In some embodiments, the DMS application running on the DMS device determines and stores potential meal markers, exercise markers, sleep markers, other activity markers, physiological conditions, other event data, etc. (e.g., secondary tracking data) based on the activity data signals from the on-body sensor assemblies (306). In some embodiments, the determination can be made by logic in the sensor devices themselves or in a separate application, e.g., running on the DMS device or a HCP computer. As will be described in more detail below, the determinations can be based upon improved data by using secondary tracking data to identify and filter out user-entered data errors and/or de-weight suspicious or potentially erroneous data. Next the DMS application responds to the determination or signals a HCP or other medical service entity to do so (308). For example, as discussed above, the DMS can ask a user to verify a meal marker, make a food choice suggestion, suggest testing BG, display carbohydrates consumed or other information, trigger a reminder, administer medication via an artificial pancreas, alert an HCP to a condition, report exercise completed information to an insurance company, or call for emergency help.

The DMS application 118 can include a data structure (e.g., a database, a hierarchy of objects, a software architecture) adapted to support the functions described above and to store information. For instance, the DMS application 118 can include a primary DMS database 400, an example of which is depicted in tabular form in FIG. 4. The example primary DMS database 400 can be populated with user-entered data regarding events or activities that the user is encouraged to log to help manage diabetes treatment. In some embodiments, the primary DMS database 400 can include a time stamp field 402, an event field 404, a state field 406, an associated secondary event ID field 408, and a weight field 410. Additional, alternative, or fewer fields can be used such as, for example, a unique event identifier field.

The time stamp field 402 is adapted to store a representation of a time and date that an associated event occurred. In some embodiments, the representation can be in the form of a start and stop time, a start and duration, or any other practicable format. The an event field 404 is adapted to store a representation of a description of the event associated with the record such as meal markers, exercise, taking medication, sleeping, etc.

The state field 406 is adapted to store a representation of a state or status of the associated record. As mentioned above, examples of states include unverified, verified, invalidated, to be reviewed, suspect, etc. "Unverified" can be used to indicate that the associated event data has not been verified but there is currently no reason to suspect the event data is not accurate. "Verified" can be used to indicate that the associated event data has been verified by a user or HCP. "Invalidated" can be used to indicate that the associated event data has been determined to be inaccurate or erroneous. "To be reviewed" can be used to indicate that there is a reason that the associated event data should be reviewed but that there is no clear indication that it is inaccurate or erroneous. "Suspect" can be used to indicate that the associated event data appears to be inaccurate or erroneous and thus should be reviewed. More or fewer states can be used.

The associated secondary event ID field 408 is adapted to store a representation of one or more secondary event identifiers that enables the DMS application to record associations between the primary DMS data and information collected and stored in the secondary tracking database discussed in detail below. In some embodiments, unique identifiers, time stamps, labels, descriptions, and/or any practicable combination of these can be used as an associated secondary event ID. In other words, the associated secondary event ID field 408 stores a list of pointers to secondary events and/or data (e.g., clock time) that are relevant to the event associated with the current record.

The weight field 410 is adapted to store a representation of a relative importance or significance assigned to the data in the associated record. The weights can be represented using a numerical value between 0 and 1 inclusive where 0 represents no weight and 1 represents full weight. In other embodiments, other values (e.g., multipliers) over different ranges can be used. In some embodiments, the different states can have automatically or predefined associated weights that reflect the relative significance of the associated event data based on the respective state. In other embodiments, the weights can be individually adjusted to reflect a confidence level in the accuracy of the associated data once the data has been cross-checked against the secondary tracking database.

The example primary DMS database 400 depicted in FIG. 4 includes three example records 412, 414, 416. It will be understood that such a primary DMS database 400 can include any number of records and the three shown are merely exemplary.

FIG. 5 depicts an example of a secondary tracking database 500 adapted to store information regarding additional data collected or generated from sources other than the user, such as from sensor assemblies or from rulesets executed programmatically against the primary DMS database 400 for example. As shown, a secondary tracking database 500 can include a number of fields, such as a time stamp field 502, a secondary event ID field 504, a secondary event field 506, and a data source field 508. Additional, alternative, or fewer fields can be included. In some embodiments, the secondary tracking database 500 can be incorporated into the primary DMS database 400 as sub-fields.

The time stamp field 502 is adapted to store a representation of a time and date that an associated secondary event occurred or was recorded. In some embodiments, the representation can be in the form of a start and stop time, a start and duration, or any other practicable format. The secondary event ID field 504 is adapted to store a representation of a unique identifier for the associated secondary event. The secondary event ID field 504 can serve as an index into the secondary tracking database 500 to allow reference (e.g., pointers) to specific events from the associated secondary event ID field 408 of the primary DMS database 400.

The secondary event field 506 is adapted to store a representation of a description of the secondary event of the associated record. Examples include any information that the sensor assemblies can provide or that can be generated via rulesets run against the primary DMS database 400. The data source field 508 is adapted to store a representation of a description of the source of the associated secondary event data. Examples include specific sensor assemblies, HCP provided data, e.g., via the Internet, ruleset generated data from the primary DMS DB, etc.

The example secondary tracking database 500 depicted in FIG. 5 includes three example records 510, 512, 514. It will be understood that such a secondary tracking database 500 can include any number of records and the three shown are merely exemplary.

The example record 412 shown in the first entry of example primary DMS database 400 indicates that the user recorded a pre-meal marker at 1:02 PM, for example by making a selection on a BGM or via an interface provided by the DMS application executing on the user's smartphone. At the time the example record 412 is created it may be assigned an Unverified state and given a weight of 1.0. At 1:09 PM, as indicated in the first record 510 of the secondary tracking database 500, a neck-worn eating sensor assembly reports that the user is eating food. The DMS application can then associate the event stored in example record 412 of the primary DMS DB based on, for example, time frame and category, with the secondary event stored in record 510 of the secondary tracking database 500 by populating the associated secondary event ID field 408 of example record 412 with "123", which is the secondary event ID field 504 value of the secondary event of record 510. At a future point, the DMS application can ask the user to confirm that the eating activity detected by the neck-worn eating sensor was in fact the meal indicated by the user-entered pre-meal marker and if so, the state of the event can be updated to Verified.

The example record 414 shown in the second entry of example primary DMS database 400 indicates that the user recorded 30 mins of exercise at 4:30 PM, for example via an interface provided by the DMS application executing on the user's smartphone. At the time the example record 414 is created it may be assigned an Unverified state and given a weight of 1.0. Previously, at 4:09 PM, as indicated in the second record 512 of the secondary tracking database 500, a heart rate monitor sensor assembly started reporting that the user's heart rate is greater than 130 bpm. The DMS application can then associate the event stored in example record 414 of the primary DMS DB based on, for example, time frame and category, with the secondary event stored in record 512 of the secondary tracking DB by populating the associated secondary event ID field 408 of example record 414 with "456", which is the secondary event ID field 504 value of the secondary event of record 512. Based on the time and duration differences however, the DMS application can mark the state of record 414 as Suspect and de-weight the value of the data down to 0.5 or, for example, a value representative of a ratio between the user-entered data and the non-user-entered data. At a future point, the DMS application can ask the user to indicate whether the start time of elevated heart rate detected by the HRM sensor should be used as the exercise start time in place of the time entered by the user. If so, the state of the event can be updated to Verified, the time stamp and duration can be corrected, and the weight raised to 1.0.

The example record 416 shown in the third entry of example primary DMS database 400 indicates that the user recorded going to sleep at 8:00 PM, for example via an interface provided by the DMS application executing on the user's smartphone. At the time the example record 416 is created, it may be assigned an Unverified state and given a weight of 1.0. However, as indicated in the third record 514 of the secondary tracking database 500, a pedometer sensor assembly started reporting that the user was walking around for an hour starting at 8:20 PM. The DMS application can then associate the event stored in example record 416 of the primary DMS DB based on, for example, time frame and category, with the secondary event stored in record 514 of the secondary tracking database 500 by populating the associated secondary event ID field 408 of example record 416 with "789", which is the secondary event ID field 504 value of the secondary event of record 514. Based on the time and typical incompatibility of sleeping while walking, the DMS application can mark the state of record 416 as Invalidated and assign a weight of 0. At a future point, the DMS application can ask the user to indicate whether the start time of the sleeping should be adjusted to after the walking was completed. If so, the state of the event can be updated to Verified, the time stamp corrected, and the weight adjusted to 1.0.

Figure 6:
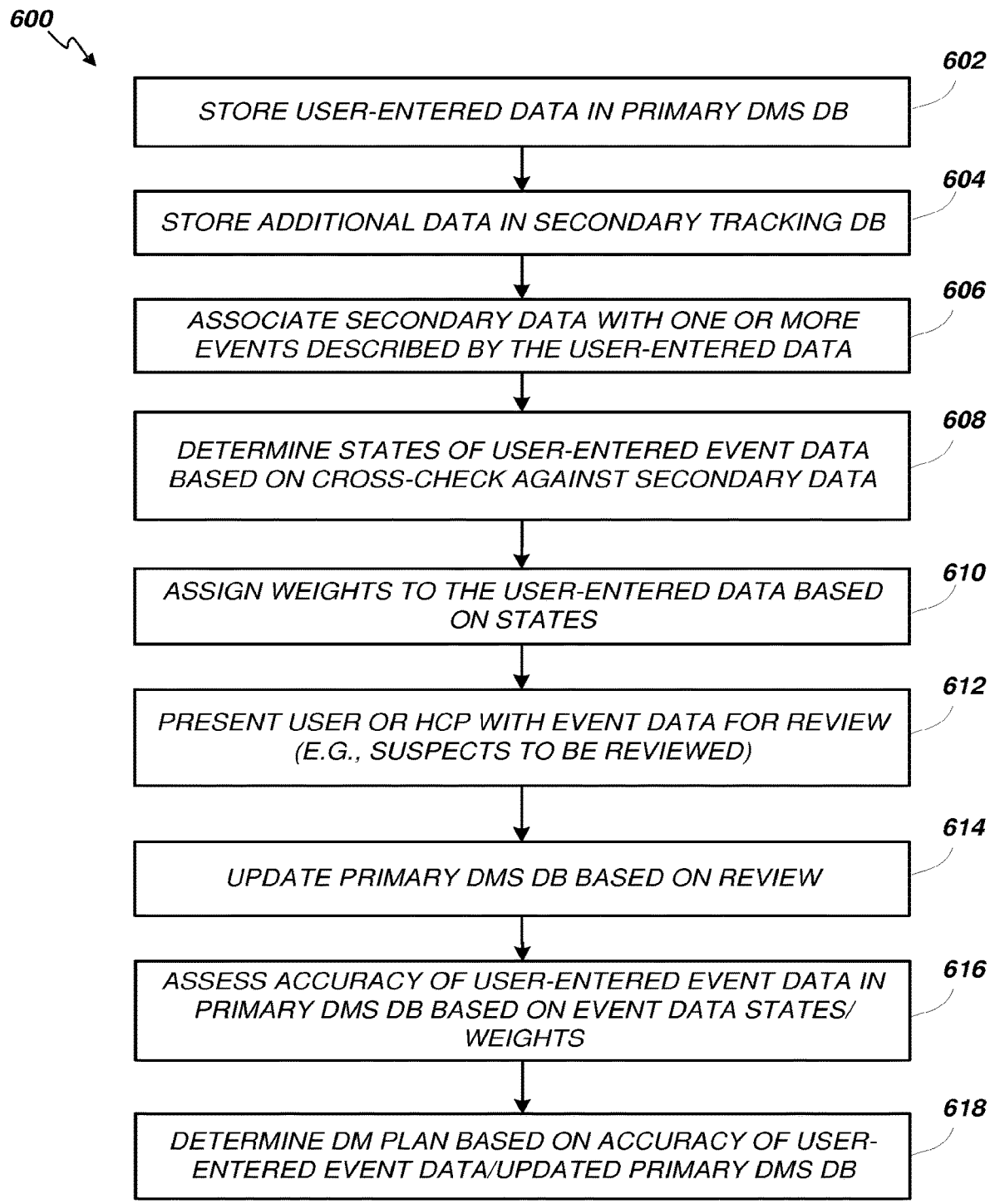
FIG. 6 is a flowchart depicting an example method of reducing user-entered data errors according to embodiments of the present invention.

Turning now to FIG. 6, an example method 600 according to embodiments of the present invention is illustrated in a flowchart. Although a particular order of steps is shown, the example method 600 can be performed in any practicable order. In addition, although a specific number of steps are shown, the example method 600 can include additional, alternative, or fewer steps.

A description of an event including, for example, a time stamp and duration is stored in a primary DMS database as user-entered data (602). The stored user-entered data can be from user-provided information, for example, via a DMS application user interface. Additional data regarding the event is stored in a secondary tracking database (604). The additional secondary data can be, for example, from sensor assemblies or generated from rulesets run against the primary DMS database.

The secondary data is associated with one or more events described by the user-entered data in the primary DMS database (606). For example, pointers to the secondary data are stored in the associated records of the primary DMS database. The associations can be based upon proximate time stamps and/or the event and the secondary data relating to the same pre-defined categories. States of the individual records of the primary DMS DB are determined based upon cross-checking the user-entered event data against the secondary data (608). The states can reflect a confidence level in the accuracy of the data. Weights can be assigned to the data records in the primary DMS DB based on the states or other considerations (610).

In some embodiments, the user or an HCP can be presented with user-entered event data for review (612) For example, the DMS application can ask the user to resolve apparent errors or inconsistencies between the primary DMS data and the secondary data. The primary DMS DB is then updated based upon the review (614). For example, data deemed inaccurate can be labeled with a state of Invalidated and/or de-weighted. The accuracy of the updated event data in the primary DMS DB can be assessed based on the states and weights assigned to each record (616). For example, lower weighted data can be given less consideration than higher weighted data. A diabetes management plan is then determined based upon the accuracy of the updated event data (618). For example, if it is determined that the user is consistently inaccurately reporting meal markers, the HCP may consider altering medication dosage or order additional tests.

Embodiments of the present invention help to seamlessly and automatically collect important diabetes management data with minimal input from the user. These embodiments further help reduce human error by using machine collected data to supplement, replace, verify, and/or validate user-entered data.

Numerous embodiments are described in this disclosure, and are presented for illustrative purposes only. The described embodiments are not, and are not intended to be, limiting in any sense. The presently disclosed inventions are widely applicable to numerous embodiments, as is readily apparent from the disclosure. One of ordinary skill in the art will recognize that the disclosed inventions may be practiced with various modifications and alterations, such as structural, logical, software, and electrical modifications. Although particular features of the disclosed inventions may be described with reference to one or more particular embodiments and/or drawings, it should be understood that such features are not limited to usage in the one or more particular embodiments or drawings with reference to which they are described, unless expressly specified otherwise.

The present disclosure is neither a literal description of all embodiments nor a listing of features of the invention that must be present in all embodiments.

The Title (set forth at the beginning of the first page of this disclosure) is not to be taken as limiting in any way as the scope of the disclosed inventions.

The term "product" means any machine, manufacture and/or composition of matter as contemplated by 35 U.S.C. § 101, unless expressly specified otherwise.

Each process (whether called a method, class behavior, algorithm or otherwise) inherently includes one or more steps, and therefore all references to a "step" or "steps" of a process have an inherent antecedent basis in the mere recitation of the term 'process' or a like term. Accordingly, any reference in a claim to a 'step' or 'steps' of a process has sufficient antecedent basis.

When an ordinal number (such as "first", "second", "third", and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

When a single device, component, structure, or article is described herein, more than one device, component, structure or article (whether or not they cooperate) may alternatively be used in place of the single device, component or article that is described. Accordingly, the functionality that is described as being possessed by a device may alternatively be possessed by more than one device, component or article (whether or not they cooperate).

Similarly, where more than one device, component, structure, or article is described herein (whether or not they cooperate), a single device, component, structure, or article may alternatively be used in place of the more than one device, component, structure, or article that is described. For example, a plurality of computer-based devices may be substituted with a single computer-based device. Accordingly, the various functionality that is described as being possessed by more than one device, component, structure, or article may alternatively be possessed by a single device, component, structure, or article.

The functionality and/or the features of a single device that is described may be alternatively embodied by one or more other devices that are described but are not explicitly described as having such functionality and/or features. Thus, other embodiments need not include the described device itself, but rather can include the one or more other devices which would, in those other embodiments, have such functionality/features.

Devices that are in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for weeks at a time. In addition, devices that are in communication with each other may communicate directly or indirectly through one or more intermediaries.

A description of an embodiment with several components or features does not imply that all or even any of such components and/or features are required. On the contrary, a variety of optional components are described to illustrate the wide variety of possible embodiments of the present invention(s). Unless otherwise specified explicitly, no component or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

Although a process may be described as including a plurality of steps, that does not indicate that all or even any of the steps are essential or required. Various other embodiments within the scope of the described invention(s) include other processes that omit some or all of the described steps. Unless otherwise specified explicitly, no step is essential or required.

Although a product may be described as including a plurality of components, aspects, qualities, characteristics and/or features, that does not indicate that all of the plurality are essential or required. Various other embodiments within the scope of the described invention(s) include other products that omit some or all of the described plurality.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a FDA" does not imply that any or all of the three items of that list are mutually exclusive and does not imply that any or all of the three items of that list are comprehensive of any category.

Headings of sections provided in this disclosure are for convenience only, and are not to be taken as limiting the disclosure in any way.

"Determining" something can be performed in a variety of manners and therefore the term "determining" (and like terms) includes calculating, computing, deriving, looking up (e.g., in a table, database or data structure), ascertaining, recognizing, associating, and the like.

A "display" as that term is used herein is an area that conveys information to a viewer. The information may be dynamic, in which case, an LCD, LED, CRT, Digital Light Processing (DLP), rear projection, front projection, or the like may be used to form the display.

The present disclosure may refer to a "control system", application, or program. A control system, application, or program, as that term is used herein, may be a computer processor coupled with an operating system, device drivers, and appropriate programs (collectively "software") with instructions to provide the functionality described for the control system. The software is stored in an associated memory device (sometimes referred to as a computer readable medium) While it is contemplated that an appropriately programmed general purpose computer or computing device may be used, it is also contemplated that hard-wired circuitry or custom hardware (e.g., an application specific integrated circuit (ASIC)) may be used in place of, or in combination with, software instructions for implementation of the processes of various embodiments. Thus, embodiments are not limited to any specific combination of hardware and software.

A "processor" means any one or more microprocessors, Central Processing Unit (CPU) devices, computing devices, microcontrollers, digital signal processors, or like devices. Exemplary processors are the INTEL PENTIUM or AMD ATHLON processors.

The term "computer-readable medium" refers to any statutory medium that participates in providing data (e.g., instructions) that may be read by a computer, a processor or a like device. Such a medium may take many forms, including but not limited to non-volatile media, volatile media, and specific statutory types of transmission media. Non-volatile media include, for example, optical or magnetic disks and other persistent memory. Volatile media include DRAM, which typically constitutes the main memory. Statutory types of transmission media include coaxial cables, copper wire and fiber optics, including the wires that comprise a system bus coupled to the processor. Common forms of computer-readable media include, for example, a floppy disk, a flexible disk, hard disk, magnetic tape, any other magnetic medium, a CD-ROM, Digital Video Disc (DVD), any other optical medium, punch cards, paper tape, any other physical medium with patterns of holes, a RAM, a PROM, an EPROM, a FLASH-EEPROM, a USB memory stick, a dongle, any other memory chip or cartridge, a carrier wave, or any other medium from which a computer can read. The terms "computer-readable memory" and/or "tangible media" specifically exclude signals, waves, and wave forms or other intangible or non-transitory media that may nevertheless be readable by a computer.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols. For a more exhaustive list of protocols, the term "network" is defined below and includes many exemplary protocols that are also applicable here.

It will be readily apparent that the various methods and algorithms described herein may be implemented by a control system and/or the instructions of the software may be designed to carry out the processes of the present invention.

Where databases and/or data structures are described, it will be understood by one of ordinary skill in the art that (i) alternative database structures to those described may be readily employed, and (ii) other memory structures besides databases may be readily employed. Any illustrations or descriptions of any sample databases/data structure presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats (including relational databases, object-based models, hierarchical electronic file structures, and/or distributed databases) could be used to store and manipulate the data types described herein. Likewise, object methods or behaviors of a database can be used to implement various processes, such as those described herein. In addition, the databases may, in a known manner, be stored locally or remotely from a device that accesses data in such a database. Furthermore, while unified databases may be contemplated, it is also possible that the databases may be distributed and/or duplicated amongst a variety of devices.

As used herein a "network" generally refers to an information or computing network that can be used to provide an environment wherein one or more computing devices may communicate with one another. Such devices may communicate directly or indirectly, via a wired or wireless medium such as the Internet, LAN, WAN or Ethernet (or IEEE 802.3), Token Ring, or via any appropriate communications means or combination of communications means. Exemplary protocols include but are not limited to: Bluetooth™, Time Division Multiple Access (TDMA), Code Division Multiple Access (CDMA), Global System for Mobile communications (GSM), Enhanced Data rates for GSM Evolution (EDGE), General Packet Radio Service (GPRS), Wideband CDMA (WCDMA), Advanced Mobile Phone System (AMPS), Digital AMPS (D-AMPS), IEEE 802.11 (WI-FI), IEEE 802.3, SAP, the best of breed (BOB), system to system (S2S), or the like. Note that if video signals or large files are being sent over the network, a broadband network may be used to alleviate delays associated with the transfer of such large files, however, such is not strictly required. Each of the devices is adapted to communicate on such a communication means. Any number and type of machines may be in communication via the network. Where the network is the Internet, communications over the Internet may be through a website maintained by a computer on a remote server or over an online data network including commercial online service providers, bulletin board systems, and the like. In yet other embodiments, the devices may communicate with one another over RF, cable TV, satellite links, and the like.

Where appropriate, encryption or other security measures such as logins and passwords may be provided to protect proprietary or confidential information.

Communication among computers and devices may be encrypted to insure privacy and prevent fraud in any of a variety of ways well known in the art. Appropriate cryptographic protocols for bolstering system security are described in Schneier, APPLIED CRYPTOGRAPHY, PROTOCOLS, ALGORITHMS, AND SOURCE CODE INC, John Wiley & Sons, Inc. 2d ed., 1996, which is incorporated by reference in its entirety.

It will be readily apparent that the various methods and algorithms described herein may be implemented by, e.g., appropriately programmed, general purpose computers and computing devices. Typically a processor (e.g., one or more microprocessors) will receive instructions from a memory or like device, and execute those instructions, thereby performing one or more processes defined by those instructions. Further, programs that implement such methods and algorithms may be stored and transmitted using a variety of media (e.g., computer readable media) in a number of manners. In some embodiments, hard-wired circuitry or custom hardware may be used in place of, or in combination with, software instructions for implementation of the processes of various embodiments. Thus, embodiments are not limited to any specific combination of hardware and software. Accordingly, a description of a process likewise describes at least one apparatus for performing the process, and likewise describes at least one computer-readable medium and/or memory for performing the process. The apparatus that performs the process can include components and devices (e.g., a processor, input and output devices) appropriate to perform the process. A computer-readable medium can store program elements appropriate to perform the method.

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicants intend to file additional applications to pursue patents for subject matter that has been disclosed and enabled but not claimed in the present application.

The foregoing description discloses only exemplary embodiments of the invention. Modifications of the above disclosed apparatus and methods that fall within the scope of the invention will be readily apparent to those of ordinary skill in the art. For example, although the examples discussed above are illustrated for a healthcare market, embodiments of the invention can be implemented for other markets.

Accordingly, while the present invention has been disclosed in connection with exemplary embodiments thereof, it should be understood that other embodiments may fall within the spirit and scope of the invention, as defined by the following claims.

The invention claimed is:

1. A method of reducing impact of user-entered data errors in a data management system (DMS), the DMS executing a DMS application on a processor to request user-entered event data from a user for an event via a DMS application interface and store the user-entered event data received from the user into a primary DMS database, the method comprising:
obtaining secondary data from at least two sensors, wherein a first sensor detects non-glucose data;
storing the secondary data into a secondary tracking database;
cross-checking the user-entered event data against the secondary data to determine whether the user-entered event data is consistent with the secondary data via the processor;
assigning a state and a weight to the user-entered event data based on a result of cross-checking, wherein the state indicates a status of the user-entered event data, and wherein the weight indicates a confidence level in an accuracy of the user-entered event data;
displaying a request to the user to review and correct or confirm the user-entered event data based on the state, wherein displaying the request includes prompting the user to indicate whether the user-entered event data are more accurate than the secondary data or whether the secondary data is more accurate than the user-entered event data;
updating the state and the weight of the user-entered event data in the primary DMS database to an updated state and an updated weight based on a user's response to the request; and
updating a diabetes management plan in response to the updated state and the updated weight assigned to the user-entered event data indicating a change in medication, testing, diet, or exercise.

2. The method of claim 1, wherein storing the user-entered event data includes prompting the user for information regarding at least one of a user's meal markers, a user's exercise, a user's medication, and a user's sleep.

3. The method of claim 1, wherein storing the secondary data includes storing data received from the DMS application generating the secondary data from the primary DMS database based on one or more rules related to the event.

4. The method of claim 1, wherein the cross-checking comprises associating the user-entered event data with the secondary data by comparing respective time stamps for the event received for the secondary data and for the user-entered event data.

5. The method of claim 1, wherein the state is at least one of "to be reviewed", "suspect", "unverified", "verified", "validated", and "invalidated".

6. The method of claim 1, wherein the weight is a numerical value.

7. The method of claim 1, wherein updating the diabetes management plan includes altering a medication dosage.

8. A data management system (DMS) comprising:
a primary DMS database accessible by a DMS application;
a secondary tracking database accessible by the DMS application;
at least one sensor assembly; and
a DMS device in communication with the at least one sensor assembly including a processor coupled to a memory, the memory operative to store instructions executable on the processor to execute the DMS application operable to:
request user-entered event data from a user regarding an event;
store the user-entered event data into the primary DMS database;
obtain secondary data from at least two sensors of the at least one sensor assembly,
wherein a first sensor detects non-glucose data;
store the secondary data into the secondary tracking database;

cross-check the user-entered event data against the secondary data to determine whether the user-entered event data is consistent with the secondary data;
assign a state and a weight to the user-entered event data based on a cross-check result,
   wherein the state indicates a status of the user-entered event data, and
   wherein the weight indicates a confidence level in an accuracy of the user-entered event data;
display a review request to the user to review and correct or confirm the user-entered event data based on the state,
   wherein displaying the review request includes prompting the user to indicate whether the user-entered event data are more accurate than the secondary data or whether the secondary data is more accurate than the user-entered event data;
update the state and the weight of the user-entered event data in the primary DMS database to an updated state and an updated weight based on a user's response to the review request; and
determine a diabetes management recommendation in response to the updated state and the updated weight assigned to the user-entered event data indicating a change in medication, testing, diet, or exercise.

9. The DMS of claim 8, wherein the review request includes prompting the user for information regarding at least one of a user's meal markers, a user's exercise, a user's medication, and a user's sleep.

10. The DMS of claim 8, wherein the secondary data further comprises results of one or more rulesets stored in the memory applied to the user-entered event data stored in the primary DMS database related to the event.

11. The DMS of claim 8, wherein cross-checking includes associating the user-entered event data with the secondary data by comparing respective time stamps for the event received with the secondary data and with the user-entered event data.

12. The DMS of claim 8, wherein the state is at least one of "to be reviewed", "suspect", "unverified", "verified", "validated", and "invalidated".

13. The DMS of claim 8, wherein the weight is a numerical value and wherein the diabetes management recommendation includes altering a medication dosage.

14. A method of reducing impact of user-entered data errors in a data management system (DMS), the DMS executing a DMS application on a processor to request user-entered event data from a user for an event regarding at least one of a user's meal markers, a user's exercise, a user's medication, and a user's sleep by prompting the user to manually enter event data, and store the user-entered event data received from the user into a primary DMS database, the method comprising:

obtaining secondary data from at least two sensors, wherein a first sensor detects biometric or physiological parameters other than blood glucose levels;
storing the secondary data into a secondary tracking database;
cross-checking the user-entered event data against the secondary data to determine whether the user-entered event data is consistent with the secondary data via the processor;
assigning a state and a weight to the user-entered event data based on a cross-checking result,
   wherein the state indicates a status of the user-entered event data, and
   wherein the weight indicates a confidence level in an accuracy of the user-entered event data;
displaying a request to the user to review and correct or confirm the user-entered event data based on the state,
   wherein the request includes prompting the user to indicate whether the user-entered event data are more accurate than the secondary data or whether the secondary data is more accurate than the user-entered event data;
updating the state and the weight of the user-entered event data in the primary DMS database to an updated state and an updated weight based on a user's response to the request;
performing a balancing analysis to assess a credibility of the user-entered event data based on a pattern of gaps detected in the user-entered event data;
updating the weight to an updated accuracy weight based on a balancing analysis result; and
updating a diabetes management plan in response to the updated accuracy weight to indicate a change in medication, testing, diet, or exercise.

15. The method of claim 14, wherein the balancing analysis determines whether to increase, decrease, maintain, or ignore the user-entered event data.

16. The method of claim 14, wherein the first sensor is an on-body sensor capable of detecting at least one of: analytes other than blood glucose, blood pressure, heart rate, pulse, wakefulness, breathing rate, respiration, body temperature, ambient temperature, pulse oximetry, humidity, electrocardiogram, movement, acceleration, proximity, direction, altitude, speed, applied force, pressure, perspiration, aging, sound, eating/drinking, snoring, bodyweight, height, and body composition.

17. The method of claim 14, wherein the secondary data includes data generated by the primary DMS database based on one or more rules related to the event.

18. The method of claim 14, wherein the state is any one of "to be reviewed", "suspect", "unverified", "verified", "validated", and "invalidated".

19. The method of claim 14, wherein the weight is a numerical value, and wherein updating the diabetes management plan includes altering a medication dosage.

* * * * *